US005118702A

United States Patent [19]

[11] Patent Number: 5,118,702

Wollweber et al.

[45] Date of Patent: Jun. 2, 1992

[54] FUNGICIDAL AND MICROBICIDAL SUBSTITUTED 1-AMINOMETHYL-3-ARYL-4-CYANO-PYRROLES

[75] Inventors: Detlef Wollweber, Wuppertal; Wolfgang Krämer, Burscheid; Wilhelm Brandes, Leichlingen; Stefan Dutzmann, Düsseldorf; Wilfried Paulus, Krefeld, all of Fed. Rep. of Germany

[73] Assignee: Bayer Aktiengesellschaft, Leverkusen, Fed. Rep. of Germany

[21] Appl. No.: 628,790

[22] Filed: Dec. 17, 1990

[30] Foreign Application Priority Data

Dec. 23, 1989 [DE] Fed. Rep. of Germany ....... 3942895
Feb. 10, 1990 [DE] Fed. Rep. of Germany ....... 4004035

[51] Int. Cl.[5] .................... A01N 43/38; C07D 207/30
[52] U.S. Cl. .................................... 514/409; 548/407
[58] Field of Search ................ 548/517, 407; 514/422, 514/409

[56] References Cited

FOREIGN PATENT DOCUMENTS 133247 7/1983 European Pat. Off. ............ 548/217
174910 9/1984 European Pat. Off. ............ 548/517
182738 10/1984 European Pat. Off. ............ 548/217
206999 6/1985 European Pat. Off. ............ 548/217
281731 1/1987 European Pat. Off. ............ 548/517
0310558 10/1987 European Pat. Off. ............ 548/517
0327977 2/1988 European Pat. Off. ............ 548/517
0327987 2/1988 European Pat. Off. ............ 548/517
3702852 1/1987 Fed. Rep. of Germany ...... 548/517
3702853 1/1987 Fed. Rep. of Germany ...... 548/517

*Primary Examiner*—Mary C. Lee
*Assistant Examiner*—Joseph K. McKane
*Attorney, Agent, or Firm*—Sprung, Horn, Kramer & Woods

[57] ABSTRACT

Fungicidal and microbicidal substituted 1-aminomethyl-3-aryl-4-cyano-pyrroles of the formula

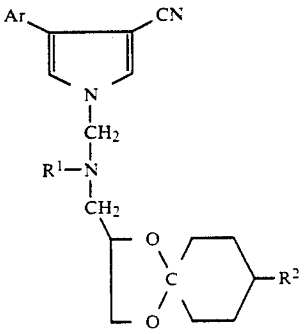

(I)

in which

Ar represents optionally substituted phenyl, $R^1$ represents optionally substituted alkyl, alkenyl, alkynyl or cycloalkyl or in each case optionally substituted aralkyl or aryl and $R^2$ represents alkyl or in each case optionally substituted cycloalkylalkyl, aralkyl, cycloalkyl or aryl, and their acid addition salts.

9 Claims, No Drawings

FUNGICIDAL AND MICROBICIDAL SUBSTITUTED 1-AMINOMETHYL-3-ARYL-4-CYANO-PYRROLES

The invention relates to new substituted 1-aminomethyl-3-aryl-4-cyano-pyrroles, to several processes for their preparation, to their use for combating pests, in particular fungi which are harmful to plants, and to their use as microbicides in the protection of materials.

It has already been disclosed that substituted 1-aminomethyl-3-aryl-4-cyano-pyrroles, such as, for example, 4-cyano-3-(2,3-dichlorophenyl)-1-(N-cyclohexyl-N-tetrahydrofurfurylaminomethyl)-pyrrole or 4-cyano-3-(2,3-dichlorophenyl)-pyrrole or 4-cyano-3-(2,3-dichlorophenyl)-1-(N,N-dimethylaminomethyl)-pyrrole have good fungicidal properties (compare, inter alia, for example EP-OS (European Published Specification) 281,731, EP-OS (European Published Specification) 174,910, EP-OS (European Published Specification) 133,247, EP-OS (European Published Specification) 182,738, EP-OS (European Published Specification) 206,999 or EP-OS (European Published Specification) 310,558).

It is furthermore known that certain sulphenamides, such as, for example, N,N-dimethyl-N'-phenyl-N'-(fluorodichloromethylsulphenyl)-sulphamide are outstandingly active, in particular against Botrytis species (compare, for example, K. H. Büchel "Pflanzenschutz und Schädlingsbekämpfung" (Plant Protection and Pest Combating), p. 141. Thieme Verlag Stuttgart 1977).

It is further already known to employ certain azolylmethylamines, such as, for example, 1,2,4-triazol-1-yl-methyl-di-n-octylamine as active compounds for combating microorganisms which can attack, damage and destroy industrial materials (compare EP-OS (European Published Specification) 106,243). Azolylmethylamines belong to the formaldehyde-eliminating compounds, i.e. their antimicrobial action is based on their capability to eliminate formaldehyde (Paulus, W., 1980. Formaldehyde releasing compounds and their utility as microbicides. Biodet. Proceed. of the IV. Internat. Symp., Pitman publishing Ltd., London, p. 307-314).

However, the activity of these previously known compounds is not completely satisfactory in all areas of application, in particular at low application rates and concentrations.

New substituted 1-aminomethyl-3-aryl-4-cyanopyrroles of the general formula (I)

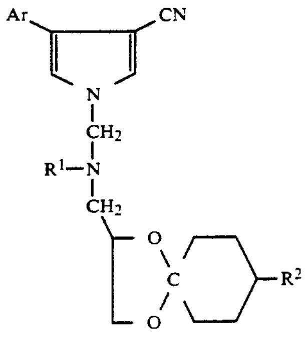

(I)

in which

Ar represents optionally substituted phenyl, $R^1$ represents optionally substituted alkyl, alkenyl, alkinyl or cycloalkyl or in each case optionally substituted aralkyl or aryl and $R^2$ represents alkyl or in each case optionally substituted cycloalkylalkyl, aralkyl, cycloalkyl or aryl, and their acid addition salts have been found.

The compounds of the formula (I) can exist as geometrical and/or optical isomers or isomer mixtures of varying composition. Both the pure isomers and the isomer mixtures are claimed according to the invention when compounds of the formula (I) are being discussed.

It has furthermore been found that the new substituted 1-aminomethyl-3-aryl-4-cyano-pyrroles of the general formula (I)

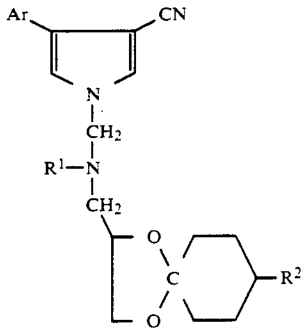

(I)

in which

Ar represents optionally substituted phenyl, $R^1$ represents optionally substituted alkyl, alkenyl, alkinyl or cycloalkyl or in each case optionally substituted aralkyl or aryl and $R^2$ represents alkyl or in each case optionally substituted cycloalkylalkyl, aralkyl, cycloalkyl or aryl, and their acid addition salts, are obtained when (a) 3-aryl-4-cyano-pyrroles of the formula (II)

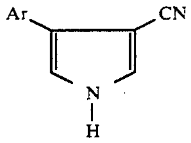

(II)

in which

Ar has the abovementioned meaning, are reacted with formaldehyde and amines of the formula (III)

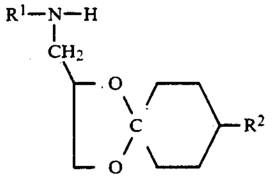

(III)

in which $R^1$ and $R^2$ have the abovementioned meanings, if appropriate in the presence of a diluent and if appropriate in the presence of a reaction auxiliary, or when (b) 3-aryl-4-cyano-pyrroles of the formula (IV)

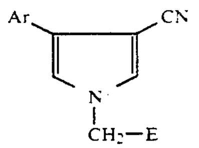

(IV)

in which

Ar has the abovementioned meaning and

E represents an electron-withdrawing leaving group, are reacted with amines of the formula (III)

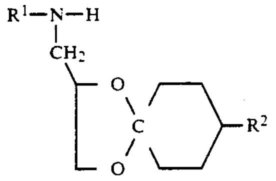

(III)

in which $R^1$ and $R^2$ have the abovementioned meanings, if appropriate in the presence of a diluent and if appropriate in the presence of an acid-binding agent and, if appropriate, an acid is then adducted or a physical separation method is added.

Finally, it has been found that the new substituted 1-amino-methyl-3-aryl-4-cyano-pyrroles of the general formula (I) have a good action against pests, in particular against fungal pests.

Surprisingly, the substituted 1-aminomethyl-3-aryl-4-cyano-pyrroles of the general formula (I) according to the invention show a better fungicidal activity in comparison to the sulphenamides known from the prior art, such as, for example, N,N-dimethyl-N,-phenyl-N'-(fluorodichloromethylsulphenyl)-sulphamide or the 3-aryl-pyrroles previously known from the prior art, such as, for example, 4-cyano-3-(2,3-dichloro-phenyl)-pyrrole or 4-cyano-3-(2, 3-dichlorophenyl)-1-(N-cyclohexyl-N-furfurylaminomethyl)-pyrrole or 4-cyano-3-(2,3-dichlorophenyl)-1-(N,N-dimethylaminomethyl)-pyrrole, which are closely related compounds chemically and/or with respect to their action.

The substituted 1-aminomethyl-3-aryl-4-cyanopyrroles of the general formula (I) according to the invention are surprisingly not only substantially more active than is to be expected in view of their content of eliminatable formaldehyde, but are also more active than the azolylmethylamines previously known from the prior art, such as, for example, 1,2,4-triazol-1-yl-methyl-din-octylamine, which is a closely related compound chemically and/or with respect to its action (compare EP 106,243). Moreover, the compounds of the formula (I) according to the invention have a wider and more balanced spectrum of action so that, compared to the prior art, they can be used advantageously as microbicides for the protection of industrial materials which, after all, can be attacked, damaged and destroyed by a large number of different species of microbes.

Formula (I) provides a general definition of the substituted 1-aminomethyl-3-aryl-4-cyano-pyrroles according to the invention. Preferred compounds of the formula (I) are those in which Ar represents phenyl which is optionally monosubstituted to polysubstituted by identical or different substituents, suitable substituents being: halogen, in each case straight-chain or branched alkyl, alkoxy, alkylthio, halogenoalkyl, halogenoalkoxy or halogenoalkylthio in each case having 1 to 4 carbon atoms and, if appropriate, 1 to 9 identical or different halogen atoms, or difluoromethylenedioxy, $R^1$ represents optionally substituted straight-chain or branched alkyl having 1 to 6 carbon atoms, suitable substituents being: cyano, cycloalkyl having 3 to 7 carbon atoms, in each case straight-chain or branched alkoxy, alkylcarbonyl, alkoxycarbonyl, alkylaminocarbonyl, dialkylaminocarbonyl, alkylsulphinyl, alkylsulphonyl or dialkylamino in each case having 1 to 6 carbon atoms in the individual alkyl moieties; additionally in each case straight-chain or branched alkenyl or alkynyl in each case having 3 to 6 carbon atoms, cycloalkyl having 3 to 7 carbon atoms or phenyl or benzyl which are optionally monosubstituted to polysubstituted by identical or different substituents in the phenyl moiety, suitable substituents in each case being: halogen, cyano, in each case straight-chain or branched alkyl, alkoxy, halogenoalkyl, halogenoalkoxy, alkylcarbonyl or alkoxycarbonyl in each case having 1 to 6 carbon atoms in the individual alkyl moieties and in the case of the halogenoalkyl or halogenoalkoxy radical in each case having 1 to 9 identical or different halogen atoms, and $R^2$ represents straight-chain or branched alkyl having 1 to 14 carbon atoms, cycloalkylalkyl or cycloalkyl in each case having 3 to 7 carbon atoms in the cycloalkyl moiety and, if appropriate, 1 to 6 carbon atoms in the straight-chain or branched alkyl moiety and in each case optionally monosubstituted to polysubstituted by identical or different substituents from the series comprising halogen and/or straight-chain or branched alkyl having 1 to 8 carbon atoms, or aralkyl or aryl in each case having 6 to 10 carbon atoms in the aryl moiety and, if appropriate, 1 to 6 carbon atoms in the straight-chain or branched alkyl moiety and in each case optionally monosubstituted to polysubstituted by identical or different substituents from the series comprising halogen and/or straight-chain or branched alkyl having 1 to 8 carbon atoms.

Particularly preferred compounds of the formula (I) are those in which

Ar represents phenyl which is optionally monosubstituted to trisubstituted by identical or different substituents, suitable substituents being: fluorine, chlorine, bromine, methyl, ethyl, n- or i-propyl, n-, i-, s- or t-butyl, methoxy, ethoxy, methylthio, trifluoromethyl, trifluoromethoxy, trifluoromethylthio or difluoromethylenedioxy, $R^1$ represents methyl, ethyl, n- or i-propyl, n-, i- or s-butyl, pentyl or hexyl, cyclohexylmethyl or cyclohexylmethyl substituted by one to three methyl groups, additionally allyl, n- or i-butenyl, propargyl, n- or i-butynyl, cyclopentyl, cyclohexyl or cyclopropyl, it being possible for these to be substituted by one to three methyl groups, or benzyl or phenyl in each case optionally monosubstituted to trisubstituted by identical or different substituents in the phenyl moiety, suitable substituents being: fluorine, chlorine, bromine, cyano, methyl, ethyl, n- or i-propyl, n-, i- or s-butyl, methoxy, ethoxy, trifluoromethyl, trifluoromethoxy, acetyl, methoxycarbonyl or ethoxycarbonyl and $R^2$ represents straight-chain or branched alkyl having 1 to 12 carbon atoms, cyclohexyl which is optionally monosubstituted to trisubstituted by identical or different substituents from the series comprising methyl, ethyl, n- or i-propyl, n-, i-, s- or t- butyl, cyclohexylalkyl having 1 to 4 carbon atoms in the straight-chain or branched alkyl moiety and optionally monosubstituted to trisubstituted in the cyclohexyl moiety by identical or different substituents from the series comprising methyl, ethyl, n- or i-propyl, n-, i-, s- or t-butyl, phenyl which is optionally monosubstituted to trisubstituted by identical or different substituents from the series comprising methyl, ethyl, n- or i-propyl, n-, i-, s- or t-butyl, or phenylalkyl having 1 to 4 carbon atoms in the straight-chain or branched alkyl moiety and optionally monosubstituted to trisubstituted in the phenyl moiety by identical or different substituents from the series comprising methyl, ethyl, n- or i-propyl, n-, i-, s- or t-butyl.

Very particularly preferred compounds of the formula (I) are those in which

Ar represents phenyl which is trisubstituted by identical or different substituents from the series comprising chlorine, fluorine, methyl, trifluoromethyl or trifluoromethoxy, $R^1$ represents ethyl, n- or i-propyl, n-, i- or s-butyl, n-pentyl, n-hexyl, allyl, propargyl, cyclohexyl, cyclopentyl, cyclohexylmethyl, methylcyclohexyl, 4-methylcyclohexylmethyl or 3-methylcyclohexylmethyl and $R^2$ represents cyclohexyl, phenyl or one of the radicals $-CH_2-R^3$, 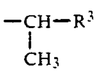 or 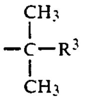

in which $R^3$ in each case represents hydrogen, methyl, ethyl, n- or i-propyl, n-, i-, s- or t-butyl, neopentyl, cyclohexyl or phenyl.

Preferred compounds according to the invention are also addition products of acids and those substituted 1-aminomethyl-3-aryl-4-cyano-pyrroles of the formula (I) in which the substituents Ar, $R^1$ and $R^2$ have the meanings which have already been mentioned for these substituents.

The acids which can be adducted and which lead to plant-tolerable addition products include, preferably, hydrohalic acids, such as, for example, hydrochloric acid and hydrobromic acid, in particular hydrochloric acid, furthermore phosphoric acid, nitric acid, mono-, bi- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, sulphonic acids, such as p-toluenesulphonic acid and 1,5-naphthalenedisulphonic acid and also saccharin or thiosaccharin.

In particular, in addition to the compounds mentioned in the Preparation Examples, the following 1-aminomethyl-3-aryl-4-cyano-pyrroles of the general formula (I) may be mentioned:

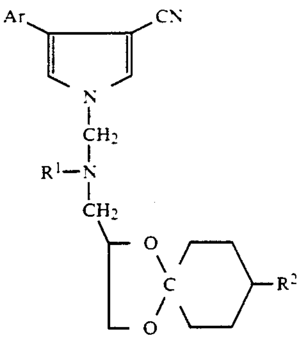

(I)

TABLE 1

| Ar | $R^1$ | $R^2$ |
|---|---|---|
| 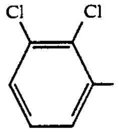 | $-C_2H_5$ | $-C(CH_3)_3$ |
| 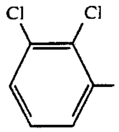 | $-(CH_2)_2-CH_3$ | $-C(CH_3)_3$ |
| 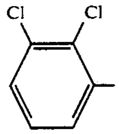 | $-CH(CH_3)_2$ | $-CH(C_2H_5)_2$ |
| 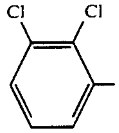 | 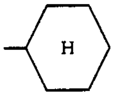 | $-CH(C_4H_9)_2$ |
| 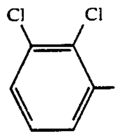 | $-CH_2CH_2-CN$ | $-C(CH_3)_3$ |
| 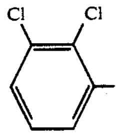 | $-CH_3$ | 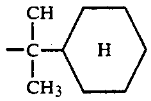 |
| 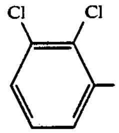 | $-CH_2CH{=}CH_2$ | $-C(CH_3)_3$ |
| 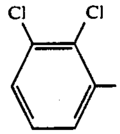 | 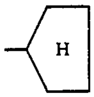 | $-C(CH_3)_3$ |

TABLE 1-continued
| Ar | $R^1$ | $R^2$ |
| --- | --- | --- |
| 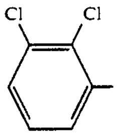 | 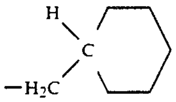 | $-CH(C_2H_5)_2$ |
| 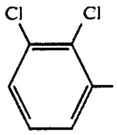 | -sec-$C_4H_9$ | 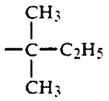 |
| 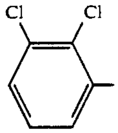 | -iso-$C_4H_9$ | $-C(CH_3)_3$ |
| 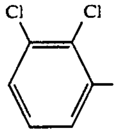 | 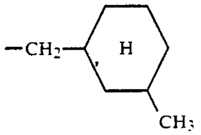 | $-C(CH_3)_3$ |
| 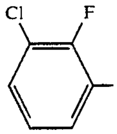 | $-C_2H_5$ | $-C(CH_3)_3$ |
| 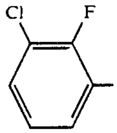 | $-(CH_2)_2-CH_3$ | $-C(CH_3)_3$ |
| 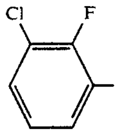 | $-CH(CH_3)_2$ | $-CH(C_2H_5)_2$ |
| 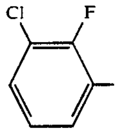 | 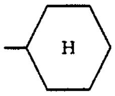 | $-CH(C_4H_9)_2$ |
| 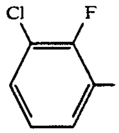 | $-CH_2CH_2-CN$ | $-C(CH_3)_3$ |
| 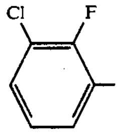 | $-CH_3$ | 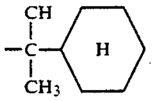 |
| 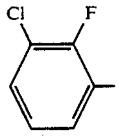 | $-CH_2CH{=}CH_2$ | $-C(CH_3)_3$ |
TABLE 1-continued
| Ar | $R^1$ | $R^2$ |
| --- | --- | --- |
| 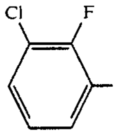 | 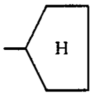 | $-C(CH_3)_3$ |
| 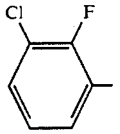 | 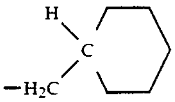 | $-CH(C_2H_5)_2$ |
| 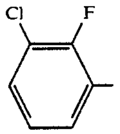 | -sec-$C_4H_9$ | 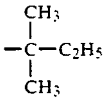 |
| 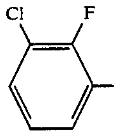 | -iso-$C_4H_9$ | $-C(CH_3)_3$ |
| 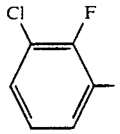 | 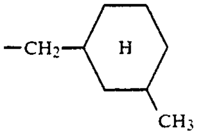 | $-C(CH_3)_3$ |
| 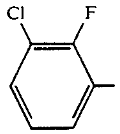 | 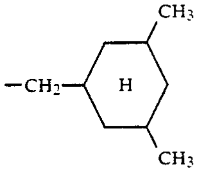 | $-C(CH_3)_3$ |
| 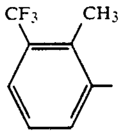 | $-C_2H_5$ | $-C(CH_3)_3$ |
| 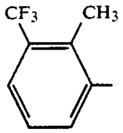 | $-(CH_2)_2-CH_3$ | $-C(CH_3)_3$ |
| 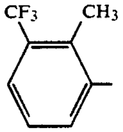 | $-CH(CH_3)_2$ | $-CH(C_2H_5)_2$ |
| 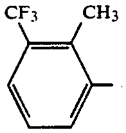 | 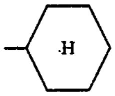 | $-CH(C_4H_9)_2$ |
| 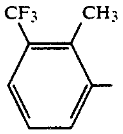 | $-CH_2CH_2-CN$ | $-C(CH_3)_3$ |

TABLE 1-continued

| Ar | $R^1$ | $R^2$ |
|---|---|---|
| 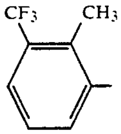 | $-CH_3$ | 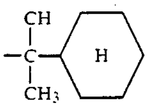 |
| 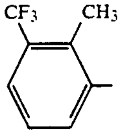 | $-CH_2CH{=}CH_2$ | $-C(CH_3)_3$ |
| 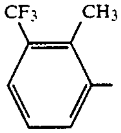 | 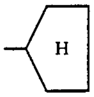 | $-C(CH_3)_3$ |
| 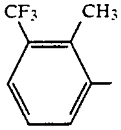 | 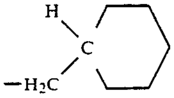 | $-CH(C_2H_5)_2$ |
| 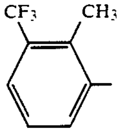 | -sec-$C_4H_9$ | 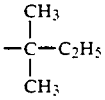 |
| 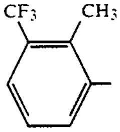 | -iso-$C_4H_9$ | $-C(CH_3)_3$ |
| 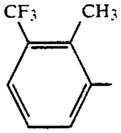 | 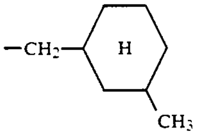 | $-C(CH_3)_3$ |
| 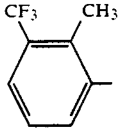 | 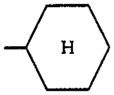 | 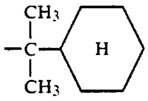 |
| 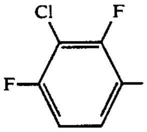 | $-C_2H_5$ | $-C(CH_3)_3$ |
| 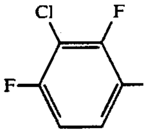 | $-(CH_2)_2-CH_3$ | $-C(CH_3)_3$ |
| 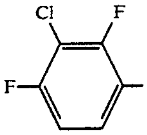 | $-CH(CH_3)_2$ | $-CH(C_2H_5)_2$ |
| 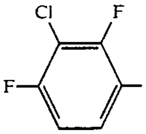 | 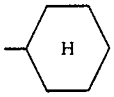 | $-CH(C_4H_9)_2$ |
| 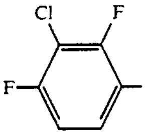 | $-CH_2CH_2-CN$ | $-C(CH_3)_3$ |
| 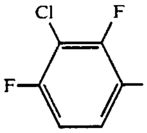 | $-CH_3$ | 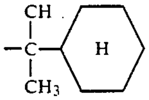 |
| 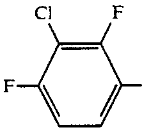 | $-CH_2CH{=}CH_2$ | $-C(CH_3)_3$ |
| 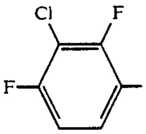 | 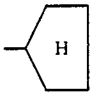 | $-C(CH_3)_3$ |
| 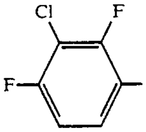 | 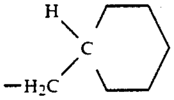 | $-CH(C_2H_5)_2$ |
| 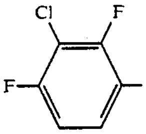 | -sec-$C_4H_9$ | 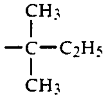 |
| 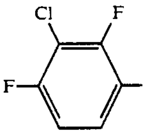 | -iso-$C_4H_9$ | $-C(CH_3)_3$ |
| 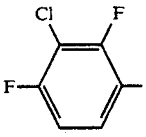 | 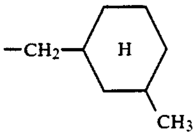 | $-C(CH_3)_3$ |
| 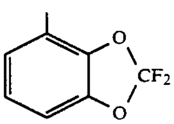 | $-C_2H_5$ | $-C(CH_3)_3$ |

If, for example, 4-cyano-3-(3-chloro-2-fluorophenyl)-pyrrole, formaldehyde and N-cyclohexyl-N-{[8-(1,1-dimethylpropyl)]-1, 4-dioxaspiro[4.5]decan-2-ylmethyl-}amine are used as starting materials, the course of the reaction of process (a) according to the invention can be represented by the following equation:

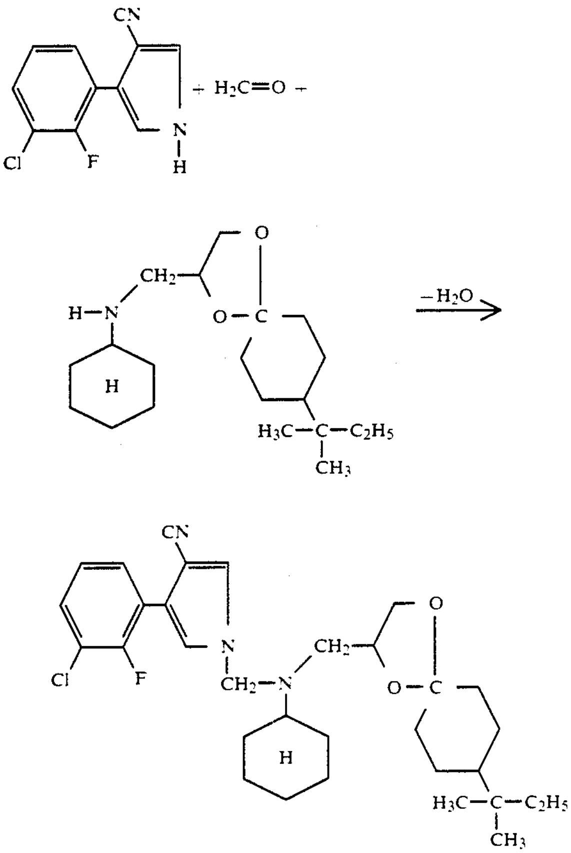

If, for example, 1-chloromethyl-4-cyano-3-(3-chloro-2-fluorophenyl)-pyrrole and N-cyclohexyl-N-{[8(1,1-dimethylpropyl)]-1, 4-dioxaspiro[4.5]decan-2-ylmethyl}-amine are used as starting materials, the course of the reaction of process (b) according to the invention can be represented by the following equation

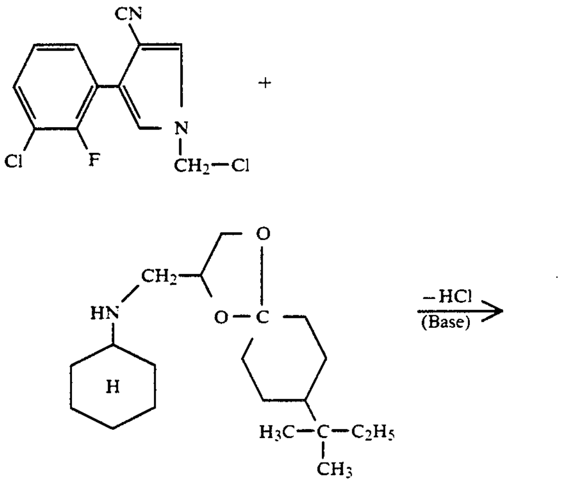

-continued

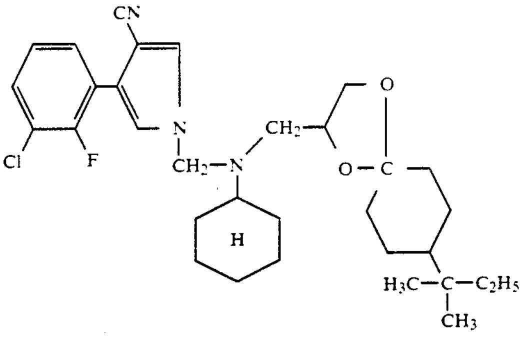

Formula (II) provides a general definition of the 3-aryl-4-cyano-pyrroles required as starting materials for carrying out process (a) according to the invention. In this formula (II), Ar preferably represents those radicals which have already been mentioned for these substituents in connection with the description of the substances of the formula (I) according to the invention.

The 3-aryl-4-cyano-pyrroles of the formula (II) are known (compare, for example, EP 174,910, EP 182,738 or EP 133,247).

Formula (IV) provides a general definition of the 3-aryl-4-cyano-pyrroles required as starting materials for carrying out process (b) according to the invention. In this formula (IV), Ar preferably represents those radicals which have already been mentioned for these substituents in connection with the description of the substances of the formula (I) according to the invention. E preferably represents hydroxyl or halogen, in particular chlorine.

The 3-aryl-4-cyano-pyrroles of the formula (IV) are also known (compare, for example, EP 133,247).

Formula (III) provides a general definition of the amines furthermore required as starting materials for carrying out processes (a) and (b) according to the invention. In this formula (III), $R^1$ and $R^2$ preferably represent those radicals which have already been mentioned in connection with the description of the substances of the formula (I) according to the invention.

The amines of the formula (III) are generally known compounds of organic chemistry or can be obtained in analogy to known processes (compare, for example, GB 1,031,916 of 2 6.1966; Org. Magnet Res 7, 488–495 [1975]; Kogyo Kagaku Zasshi 63, 1593–1597 [1960] and CA 60: 10 542 f).

Suitable diluents for carrying out process (a) according to the invention are inert organic solvents or aqueous systems. Protic solvents are preferably used, for example alcohols, such as methanol, ethanol or propanol or carboxylic acids, such as formic acid, acetic acid or propionic acid or their mixtures with water. It is also possible to carry out process (a) according to the invention in aprotic solvents. In particular, these include aliphatic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene one, nitriles, such as acetonitrile or propionitrile, amides, such as dimethylformamide, dimethylacetamide, N-methylformanilide, N-methylpyrrolidone or hexamethylphosphoramide, esters, such as ethyl acetate, or sulphoxides, such as dimethyl sulphoxide Process (a) according to the invention is optionally carried out in the presence of a suitable reaction auxiliary. For this purpose, either catalytic to equimolar amounts of an organic or inorganic acid or corresponding amounts of a suitable base are suitable.

Suitable acidic reaction auxiliaries are, in particular, organic mineral acids, such as phosphoric acid, sulphuric acid, nitric acid, hydrochloric acid or hydrobromic acid or organic acids, such as formic acid, acetic acid, propionic acid, methanesulphonic acid, benzenesulphonic acid or toluenesulphonic acid.

Suitable basic reaction auxiliaries are all customary inorganic or organic bases These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU)

However, it is also possible simultaneously to use as a reaction auxiliary in an appropriate excess the amine of the formula (III) used as a reaction component.

The reaction temperatures can be varied within a relatively wide range when carrying out process (a) according to the invention In general, the process is carried out at temperatures between 0° C. and 120° C., preferably at temperatures between 20° C. and 90° C.

In order to carry out process (a) according to the invention, 1.0 to 2.0 moles, preferably 1.0 to 1.5 moles of amine of the formula (III) and 1.0 to 2.0 moles, preferably 1.0 to 1.5 moles of formaldehyde are in general employed per mole of 3-aryl-4-cyanopyrrole of the formula (II). The formaldehyde is employed either in the form of an aqueous solution, as paraformaldehyde or as 1,3,5-trioxane An aqueous solution is preferably used.

The reaction is carried out and the reaction products of the formula (I) are worked up and isolated in analogy to known processes (compare EP 133,247)

Suitable diluents for carrying out process (b) according to the invention are inert organic solvents.

In particular, these include aliphatic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoramide, esters, such as ethyl acetate, or sulphoxides, such as dimethyl sulphoxide.

Process (b) according to the invention is optionally carried out in the presence of a suitable acidbinding agent. Those which are suitable are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

However, it is also possible simultaneously to employ as a reaction auxiliary in an appropriate excess the amine of the formula (III) suitable as a reaction component.

The reaction temperatures can be varied within a relatively wide range when carrying out process (b) according to the invention In general, the process is carried out at temperatures between 0° C. and 100° C., preferably at temperatures between 20° C. and 60° C.

In order to carry out process (b) according to the invention, 1.0 to 2.0 moles, preferably 1.0 to 1.5 moles of amine of the formula (III) and optionally 1.0 to 2.0 moles, preferably 1.0 to 1.5 moles of acidbinding agent are in general employed per mole of 3-aryl-4-cyanopyrrole of the formula (IV) The reaction is carried out and the reaction products of the formula (I) are worked up and isolated in analogy to known processes.

The active compounds according to the invention have a strong action against pests and can be employed practically for combating undesired harmful organisms. The active compounds are suitable, for example, for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;* Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (condiia form: Drechslera, syn: Helminthosporium):

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, Tilletia caries;

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea:*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;*
Pseudocercosporella species, such as, for example, *Pseudocercosporella herpotrichoides* and
Sclerotinia species, such as, for example, *Sclerotinia sclerotiorum.*

The good toleration, by plants, of the active compounds, at the concentrations required for combating plant diseases, permits treatment of above-ground parts of plants, of vegetative propagation stock and seeds, and of the soil.

In this connection, the active compounds according to the invention can be employed protectively with particularly good effect for combating Botrytis in beans, Sphaerotheca in cucumbers and Leptosphaeria in wheat. The very good activity in combating Fusarium culmorum in the seed treatment of wheat is additionally to be emphasized.

The compounds according to the invention moreover also show a good fungicidal action against Erysiphe graminis on cereal species and against Pellicularia on rice as well as a good in vitro action.

Depending on their particular physical and/or chemical properties, the active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The active compounds according to the invention are additionally distinguished by a wide and potent microbicidal action and by remarkably good activity against algae and slime organisms. The substances according to the invention are therefore excellent for the protection of industrial materials.

Industrial materials are, according to the invention, non-living materials which have been prepared for use in industry For example, industrial materials which are intended to be protected from microbial change or destruction by active compounds according to the invention can be adhesives, sizes, paper and cardboard, textiles, leather, wood, paints and plastic articles, cooling lubricants and other materials which can be attacked or decomposed by microorganisms. In the context of the materials to be protected, parts of production plants, for example cooling water circulations, which can be impaired by replication of microorganisms may be mentioned. In the context of the present invention, preferably adhesives, sizes, paper and cardboard, leather, wood, paints, cooling lubricants and cooling circulations may be mentioned as industrial materials.

Microorganisms which can cause degradation of or a change in the industrial materials and which may be mentioned are, for example, bacteria, fungi, yeasts, algae and slime organisms. The active compounds according to the invention preferably act against fungi, in particular mold fungi, wood-discolouring and wood-destroying fungi (Basidiomycetes), and against slime organisms and algae.

Examples of microorganisms of the following orders may be mentioned:

Alternaria, such as *Alternaria tenuis,*
Aspergillus, such as *Aspergillus niger,*
Chaetomium, such as *Chaetomium globosum,*
Coniophora, such as Coniophora puteana,
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,*
Staphylococcus, such as *Staphylococcus aureus.*

Depending on the area of application, an active compound according to the invention can be converted into the customary formulations, such as solutions, emulsions, suspensions, powders, pastes and granules.

These can be prepared in a manner known per se, for example by mixing the active compounds with an extender which consists of a liquid solvent and/or solid carriers, if appropriate using surface-active agents, such as emulsifiers and/or dispersants, it being possible, if appropriate, in the case of the use of water as an extender to use organic solvents such as alcohols as auxiliaries.

Liquid solvents for the active compounds may be, for example, water, alcohols, such as lower aliphatic alcohols, preferably ethanol or isopropanol, or benzyl alcohol, ketones, such as acetone or methyl ethyl ketone, liquid hydrocarbons, such as benzine fractions, or halogenated hydrocarbons, such as 1,2-dichloroethane.

Microbicidal agents in general contain the active compounds in an amount of from 1 to 95%, preferably of from 10 to 75%.

The application concentrations of the active compounds according to the invention depend on the type and the occurrence of the microorganisms to be combated, and on the composition of the material to be protected. The optimum application quantity can be determined by a series of tests. In general, the application concentrations are in the range from 0.001 to 5% by weight, preferably from 0.05 to 1.0% by weight, relative to the material to be protected.

The active compounds according to the invention may also be present in a mixture with other known active compounds. Examples which may be mentioned are the following active compounds: benzyl alcohol mono(poly)hemiformal and other formaldehyde-eliminating compounds, benzimidazolyl methylcarbamates, tetramethylthiuram disulphide, zinc salts of dialkyl dithiocarbamates, 2,4,5,6-tetrachloroisophthalonitrile, thiazolylbenzimidazole, mercaptobenzothiazole, 2-thiocyanatomethylthiobenzothiazole, organotin compounds, methylene bisthiocyanate, N-alkyl- and N-aryliodopropargyl carbamates, triazole and imidazole fungicides, phenol derivatives, such as 2-phenylphenol, (2,2'-dihydroxy-5,5'-dichloro)diphenylmethane and 3-methyl-4-chloro-phenol.

The preparation and the use of the active compounds according to the invention can be seen from the following examples:

PREPARATION EXAMPLES

Example 1

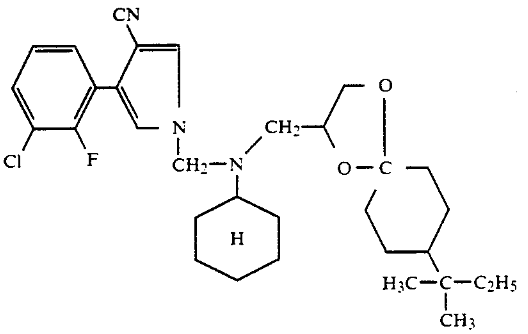

0.6 g (9.697 mmol) of 37 per cent strength aqueous formaldehyde solution and 0.1 ml of glacial acetic acid are added to 2.0 g (9.064 mmol) of 4-cyano-3-(2-fluoro-3-chlorophenyl)-pyrrole in 10 ml of ethanol. 3.1 g (9.697 mmol) of N-cyclohexyl-[8-(1,1-dimethylpropyl)-1, 4-dioxaspiro[4.5]decane]-2-methaneamine are then added dropwise with stirring and, after addition is complete, the mixture is stirred for 20 hours at room temperature. For working up, 50 ml of ethyl acetate are added, the mixture is washed three times with water, dried over sodium sulphate, the solvent is removed in vacuo and the residue is recrystallized from ether/cyclohexane.

4-Cyano-3-(2-fluoro-3-chlorophenyl)-1-(N-cyclohexyl-1, 4-dioxaspiro[4.5]decane-8-(1,1-dimethylpropyl)-2-methaneaminomethyl)-pyrrole is obtained in quantitative yield as a brown oil.

The final products of the formula (I)

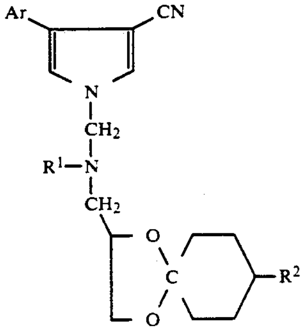

(I)

listed below in Table 2 are obtained in an analogous manner to Example 1 and taking into account the instructions in the descriptions of the processes according to the invention:

TABLE 2

| Ex. No. | Ar | $R^1$ | $R^2$ |
|---|---|---|---|
| 2 | 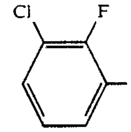 | 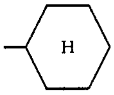 | 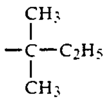 |
| 3 | 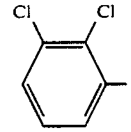 | 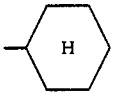 | 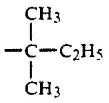 |
| 4 | 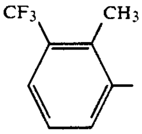 | $-C_4H_9$-n | 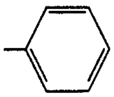 |
| 5 | 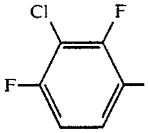 | $-CH_2CH_2-OCH_3$ | 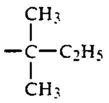 |
| 6 | 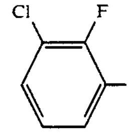 | $-CH_2CH_2-OCH_3$ | 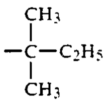 |
| 7 | 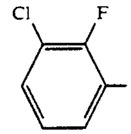 | $-(CH_2)_3-OCH_3$ | $-C(CH_3)_3$ |
| 8 | 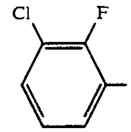 | $-C_4H_9$-n | 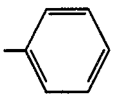 |
| 9 | 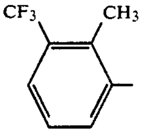 | $-C_5H_{11}$-n | $-CH(C_2H_5)_2$ |
| 10 | 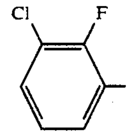 | $-C_5H_{11}$-n | $-CH(C_2H_5)_2$ |

TABLE 2-continued

| Ex. No. | Ar | $R^1$ | $R^2$ |
|---|---|---|---|
| 11 | 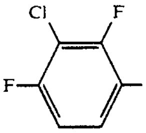 | $-C_5H_{11}$-n | $-CH(C_2H_5)_2$ |
| 12 | 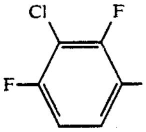 | $-(CH_2)_3-OCH_3$ | $-C(CH_3)_3$ |
| 13 | 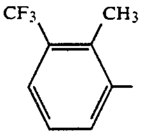 | $-(CH_2)_3-OCH_3$ | $-C(CH_3)_3$ |
| 14 | 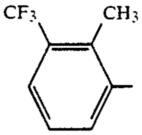 | $-(CH_2)_2-OCH_3$ | 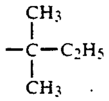 . |
| 15 | 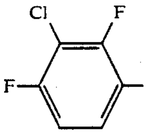 | 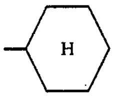 | 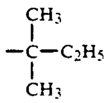 |
| 16 | 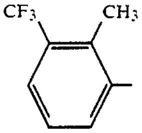 | 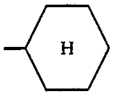 | 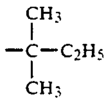 |
| 17 | 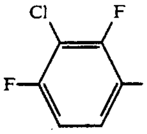 | $-C_4H_9$-n | 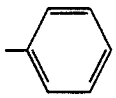 |

The compounds of Examples 1 to 17 are produced in the form of viscous oils. They are identified by means of $^1$H-NMR.

The $^1$H-NMR spectra were recorded in deuterochloroform ($CDCl_3$) using tetramethylsilane (TMS) as the internal standard.

For the physical data for the preparative examples, see Table 3 which follows:

TABLE 3
| Ex. No. | Structure | physical constants $^{1}H$-NMR data in $CDCl_3$ (300 MHz) δ |
|---|---|---|
| 1) | 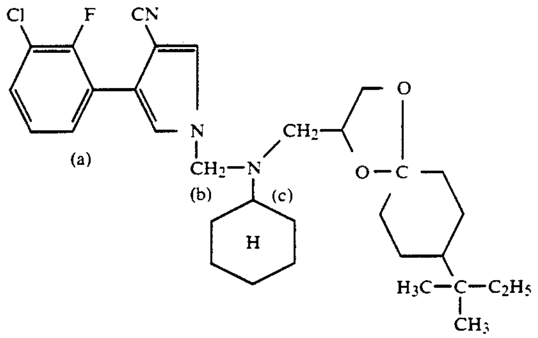 | a(CH) = 7.73 M<br>b($CH_2$) = 4.87 M<br>c(CH) = 2.6 M |
| 2) | 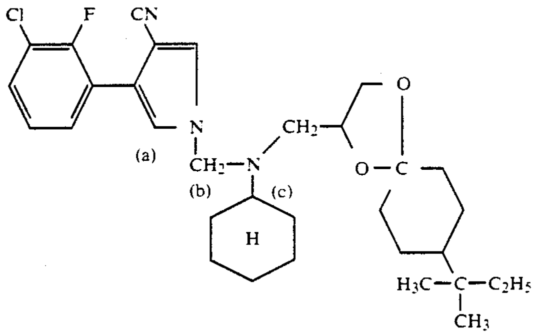 | a(CH) = 7.2 S<br>b($CH_2$) = 4.88 M<br>c(CH) = 2.59 M |
| 3) | 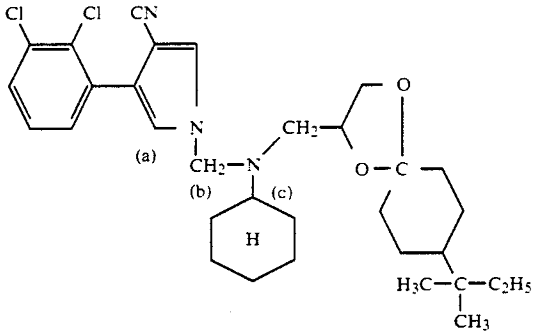 | a(CH) = 7.08 S<br>b($CH_2$) = 4.90 M<br>c(CH) = 2.58 M |
| 4) | 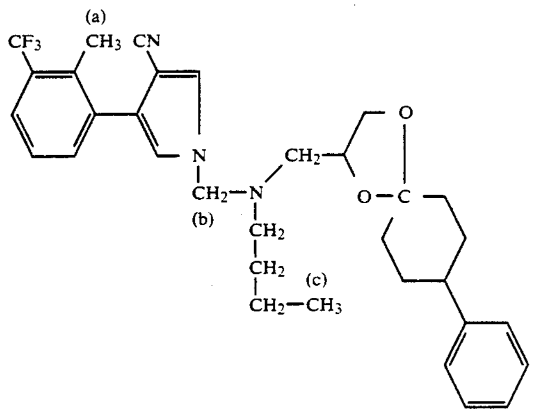 | a($CH_3$) = 2.40 S<br>b($CH_2$) = 4.89 M<br>c($CH_3$) = 0.90 M(T) |

TABLE 3-continued
| Ex. No. | Structure | physical constants $^1$H-NMR data in $CDCl_3$ (300 MHz) δ |
|---|---|---|
| 5) | 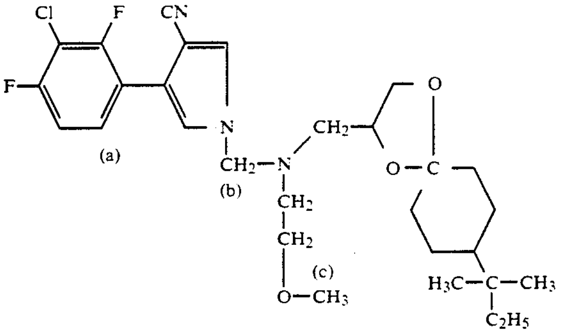 | a(CH) = 7.65 M<br>b($CH_2$) = 4.98 M<br>c($CH_3$) = 3.35 S |
| 6) | 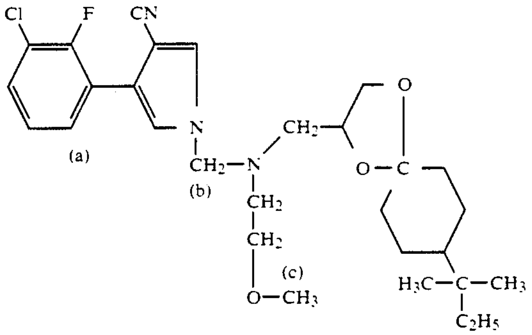 | a(CH) = 7.75 M<br>b($CH_2$) = 5.01 M<br>c($CH_3$) = 3.35 S |
| 7) | 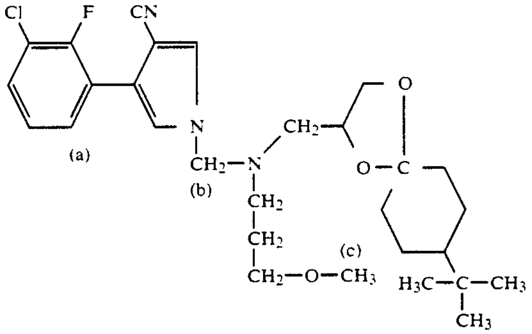 | a(CH) = 7.75 M<br>b($CH_2$) = 4.92 M<br>c($CH_3$) = 3.30 S |
| 8) | 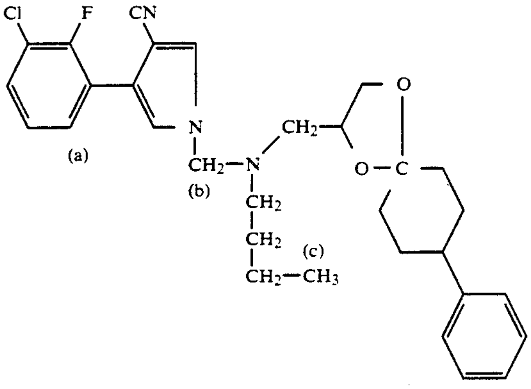 | a(CH) = 7.75 M<br>b($CH_2$) = 4.93 M<br>c($CH_3$) = 0.86 M |

TABLE 3-continued
| Ex. No. | physical constants<br>Structure | $^1$H-NMR data in CDCl$_3$ (300 MHz) δ |
|---|---|---|
| 9) | 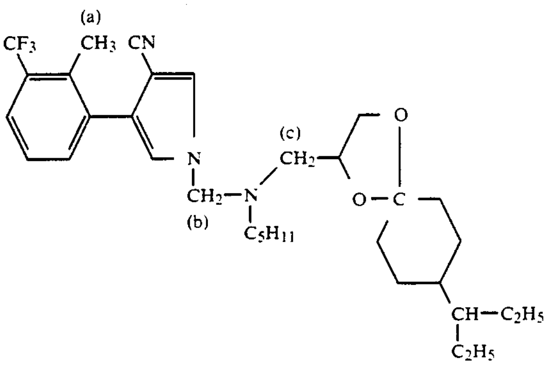 | a(CH$_3$) = 2.41 S<br>b(CH$_2$) = 4.88 M<br>c(CH$_2$) = 2.63 M |
| 10) | 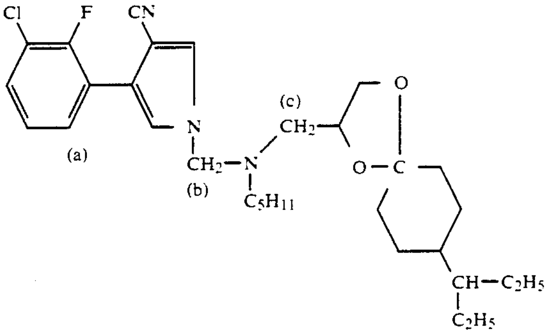 | a(CH) = 7.72 M<br>b(CH$_2$) = 4.91 M<br>c(CH$_2$) = 2.59 M |
| 11) | 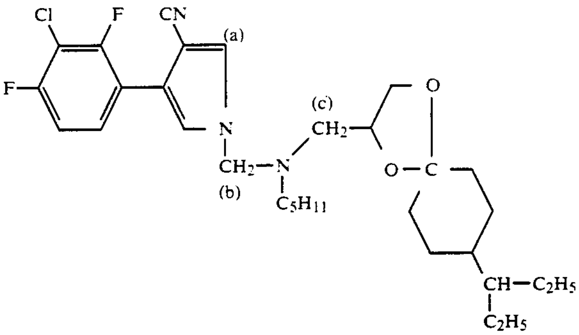 | a(CH) = 7.38 S<br>b(CH$_2$) = 4.87 M<br>c(CH$_2$) = 2.65 M |
| 12) | 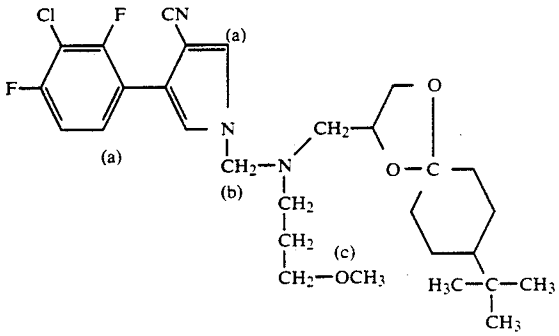 | a(CH) = 7.4 S<br>b(CH$_2$) = 4.91 M<br>c(CH$_3$) = 3.32 S |

TABLE 3-continued
| Ex. No. | Structure (physical constants) | $^1$H-NMR data in $CDCl_3$ (300 MHz) δ |
|---|---|---|
| 13) | 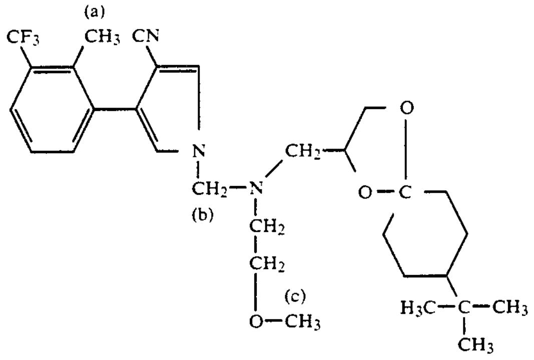 | a($CH_3$) = 2.45 S<br>b($CH_2$) = 4.88 M<br>c($CH_3$) = 3.3 S |
| 14) | 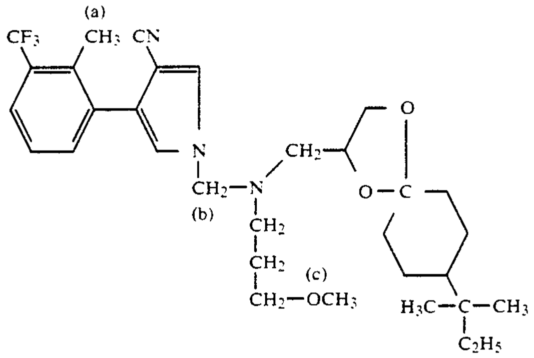 | a($CH_3$) = 2.42 S<br>b($CH_2$) = 4.98 M<br>c($CH_3$) = 3.35 S |
| 15) | 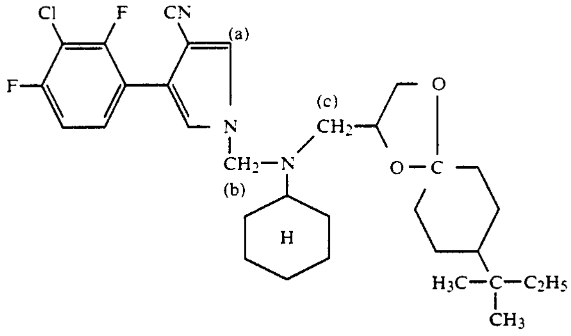 | a(CH) = 7.43 S<br>b($CH_2$) = 4.88 M<br>c($CH_2$) = 2.8 M |
| 16) | 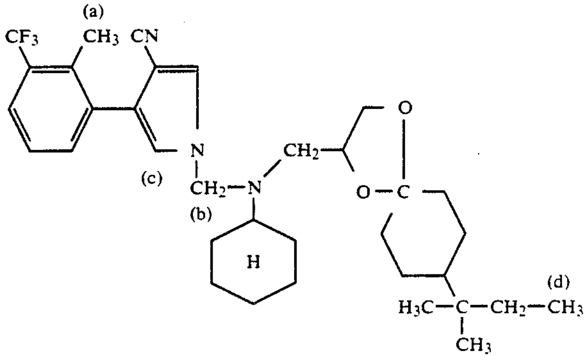 | a($CH_3$) = 2.42 S<br>b($CH_2$) = 4.88 M<br>c(CH) = 6.78 S<br>d($CH_3$) = 0.8 M(T) |

TABLE 3-continued

| Ex. No. | physical constants Structure | $^1$H-NMR data in $CDCl_3$ (300 MHz) δ |
|---|---|---|
| 17) | 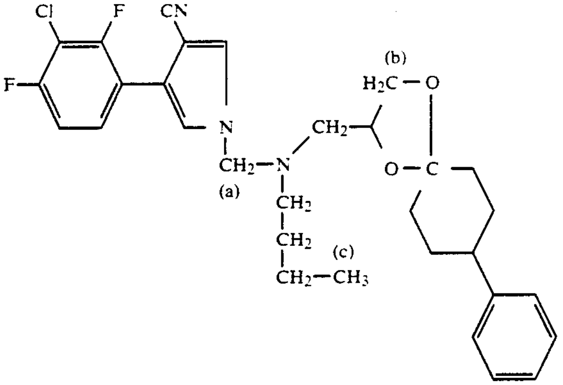 | a($CH_2$) = 4.9 M<br>b($CH_2$) = 3.68 M<br>c($CH_3$) = 0.9 M(T) |

M = multiplet
S = singlet
(T) = triplet character

Use Examples

In the following Use Examples, the compounds shown below were employed as comparison substances:

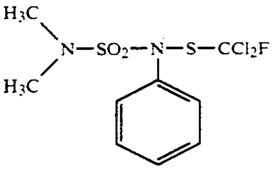
(A)

N,N-dimethyl-N'-(fluorodichloromethylsulphenyl)sulphamide

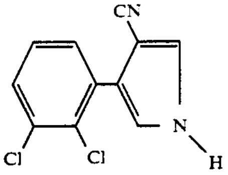
(B)

4-cyano-3-(2,3-dichlorophenyl)-pyrrole (disclosed in EP 174,910)

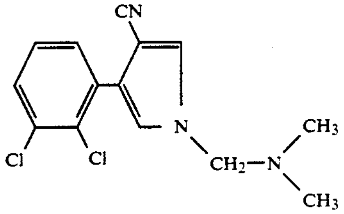
(C)

4-cyano-3-(2,3-dichlorophenyl)-1-(N,N-dimethylaminomethyl)-pyrrole (disclosed in EP 133,247 and EP 182,738).

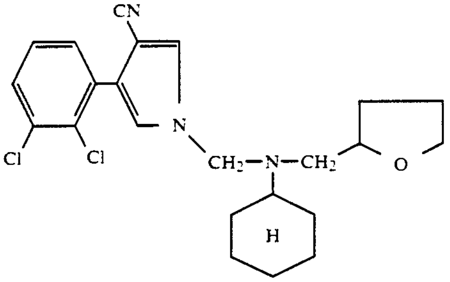
(D)

4-cyano-3-(2,3-dichloro-phenyl)-1(N-cyclohexyl-N-tetrahydrofurfurylaminomethyl)-pyrrole (disclosed in EP 281,731)

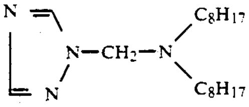
(E)

1,2,4-triazol-1-yl-methyl-di-n-octylamine (disclosed in EP 106,243).

Example A

Botrytis test (bean)/protective

| | |
|---|---|
| Solvent: | 4.7 parts by weight of acetone |
| Emulsifier: | 0.3 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after the inoculation, the size of the infected spots on the leaves is evaluated.

In this test, a clearly superior activity compared with the prior art is shown, for example, by the compound according to Preparation Example 1.

Example B

Sphaerotheca test (cucumber) / protective

| | |
|---|---|
| Solvent: | 4.7 parts by weight of acetone |
| Emulsifier: | 0.3 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus Sphaerotheca fuliginea.

The plants are then placed in a greenhouse at 23° to 24° C. and at a relative atmospheric humidity of about 75%.

Evaluation is carried out 10 days after the inoculation.

In this test, a clearly superior activity compared with the prior art is shown, for example, by the compounds according to Preparation Examples 1. 2 and 3.

Example C

Leptosphaeria nodorum test (wheat)/protective

| | |
|---|---|
| Solvent: | 100 parts by weight of dimethylformamide |
| Emulsifier: | 0.25 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is carried out 10 days after the inoculation.

In this test, a clearly superior activity compared with the prior art is shown, for example, by the compound according to Preparation Example 1.

Example D

Fusarium culmorum test (wheat) / seed treatment

The active compounds are applied as dry dressings. They are prepared by extending the particular active compound with ground mineral to give a finely pulverulent mixture which ensures a uniform distribution on the seed surface.

For dressing, the infected seed is shaken for 3 minutes with the dressing in a closed glass bottle.

The wheat is sown using 2×100 grains 1 cm deep in a standard soil and cultivated in a greenhouse at a temperature of about 18° C. in seed boxes which are exposed to light for 15 hours daily.

About 3 weeks after sowing, the plants are evaluated for symptoms.

In this test, a clearly superior activity compared with the prior art is shown, for example, by the compound according to Preparation Example 1.

Example E

Minimum inhibitory concentration

In order to demonstrate the activity against fungi, the minimum inhibitory concentrations (MIC) of active compounds according to the invention are determined;

Active compounds according to the invention are added in concentrations of 0.1 mg/l to 5,000 mg/l to an agar which has been prepared from beer wort and peptone. After solidification of the agar, it is contaminated with pure cultures of the test organisms shown in the table. The MIC is determined after storage for 2 weeks at 28° C. and at 60 and 70% relative atmospheric humidity. The MIC is the lowest concentration of active compound at which no growth at all takes place as a result of the species of microbe used. With many of the compounds according to the invention, it is between 20 and 50 mg/l.

It is understood that the specification and examples are illustrative but not limitative of the present invention and that other embodiments within the spirit and scope of the invention will suggest themselves to those skilled in the art.

We claim:

1. A substituted 1-aminomethyl-3-aryl-4-cyano-pyrrole of the formula

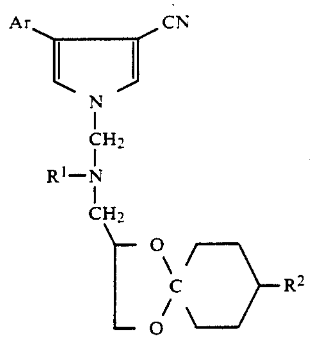

(I)

in which

Ar represents phenyl which is optionally substituted by substituents independently selected from the group consisting of halogen, in each case straight-chain or branched alkyl, alkoxy, alkylthio, halogenalkyl, halogenalkoxy or halogenoalkylthio in each case having 1 to 4 carbon atoms and, if appropriate, 1 to 9 identical or different halogen atoms, and difluoromethylenedioxy, represents straight-chain or branched alkyl having 1 to 6 carbon atoms and optionally substituted by cyano, cycloalkyl having 3 to 7 carbon atoms, in each case straight-chain or branched alkoxy, alkylcarbonyl, alkoxycarbonyl, alkylaminocarbonyl, dialkylaminocarbonyl, alkylsulphinyl, alkylsulphonyl or dialkylamino in each case having 1 to 6 carbon atoms in the individual alkyl moieties; or straight-chain or branched alkenyl or alkynyl in each case having 3 to 6 carbon atoms, cycloalkyl having 3 to 7 carbon atoms or phenyl or benzyl which are optionally substituted in the phenyl moiety by substituents independently selected from the group consisting of halogen, cyano, and in each case straight-chain or branched alkyl, alkoxy, halogenoalkyl, halogenoalkoxy, alkylcarbonyl or alkoxycarbonyl in each case having 1 to 6 carbon atoms in the individual alkyl moieties and in the case of the halogenoalkyl or halogenoalkoxy radical in each case having 1 to 9 identical or different halogen atoms, and represents straight-chain or branched alkyl having 1 to 14 carbon atoms, cycloalkylalkyl or cycloalkyl in each case having 3 to 7 carbon atoms in the cycloalkyl moiety and, if appropriate, 1 to 6 carbon atoms in the straight-chain or branched alkyl moiety and in each case optionally monosubstituted to polysubstituted by identical or different substituents from the group consisting of halogen and straight-chain or branched alkyl having 1 to 8 carbon atoms, aralkyl or aryl in each case having 6 to 10 carbon atoms in the aryl moiety and, if appropriate, 1 to 6 carbon atoms in the straight-chain or branched alkyl moiety and in each case optionally monosubstituted to polysubstituted by identical or different substituents from the group consisting of halogen and straight-chain or branched alkyl having 1 to 8 carbon atoms, or an acid addition salt thereof.

2. A substituted 1-aminomethyl-3-aryl-4-cyano-pyrrole according to claim 1, in which Ar represents phenyl which is optionally monosubstituted to trisubstituted by identical or different substituents from the group consisting of fluorine, chlorine, bromine, methyl, ethyl, n- or i-propyl, n-, i-, s- or t-butyl, methoxy, ethoxy, methylthio, trifluoromethyl, trifluoromethoxy, trifluoronethylthio and difluoromethylenedioxy, $R^1$ represents methyl, ethyl, n- or i-propyl, n-, i- or s-butyl, -pentyl or hexyl, cyclohexylmethyl or cyclohexylmethyl substituted by one to three methyl groups, or allyl, n- or i-butenyl, propargyl, n- or i-butynyl, cyclopentyl, cyclohexyl cr cyclopropyl, it being possible for these to be substituted by one to three methyl groups, or benzyl or phenyl in each case optionally monosubstituted to trisubstituted in the phenyl moiety by identical or different substituents selected from the group consisting of fluorine, chlorine, bromine, cyano, methyl, ethyl, n- or i-propyl, n-, i- or 2-butyl, methoxy, ethoxy, trifluoromethyl, trifluoromethoxy, acetyl, methoxycarbonyl and ethoxycarbonyl and $R^2$ represents straight-chain or branched alkyl having 1 to 12 carbon atoms, cyclohexyl which is optionally monosubstituted to trisubstituted by identical or different substituents from the group consisting of methyl, ethyl, n- or i-propyl, n-, i-, s- or t- butyl, cyclohexylalkyl having 1 to 4 carbon atoms in the straight-chain or branched alkyl moiety and optionally monosubstituted to trisubstituted in the cyclohexyl moiety by identical or different substituents from the group consisting of methyl, ethyl, n- or i-propyl, n-, i-, s- or t-butyl, phenyl which is optionally monosubstituted to trisubstituted by identical or different substituents from the group consisting of methyl, ethyl. n- or i-propyl, n-, i-, s- or t-butyl, and phenylalkyl having 1 to 4 carbon atoms in the straight-chain or branched alkyl moiety and optionally monosubstituted to trisubstituted in the phenyl moiety by identical or different substituents from the group consisting of methyl, ethyl, n- or i-propyl, and n-, i-, s- or t-butyl, or an acid addition salt thereof.

3. A substituted 1-aminomethyl-3-aryl-4-cyano-pyrrole according to claim 1, in which Ar represents phenyl which is trisubstituted by identical or different substituents from the group consisting of chlorine, fluorine, methyl, trifluoromethyl trifluoromethoxy, $R^1$ represents ethyl, n- or i-propyl, n-, i- or s-butyl, n-pentyl, n-hexyl, allyl, propargyl, cyclohexyl, cyclopentyl, cyclohexylmethyl, methylcyclohexyl, 4-methylcyclohexylmethyl or 3-methylcyclohexylmethyl and $R^2$ represents cyclohexyl, phenyl or one of the radicals

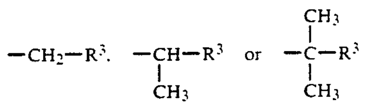

in which $R^3$ in each case represents hydrogen, methyl, ethyl, n- or i-propyl, n-, i-, s- or t-butyl, neopentyl, cyclohexyl or phenyl, or an acid addition salt thereof.

4. A compound according to claim 1, wherein such compound is 4-cyano-3-(2-fluoro-3-chlorophenyl)-1-(N-cyclohexyl-1, 4-dioxaspiro[4.5]decane-8-(1,1-dimethylpropyl)-2-ethaneaminomethyl)-pyrrole of the formula

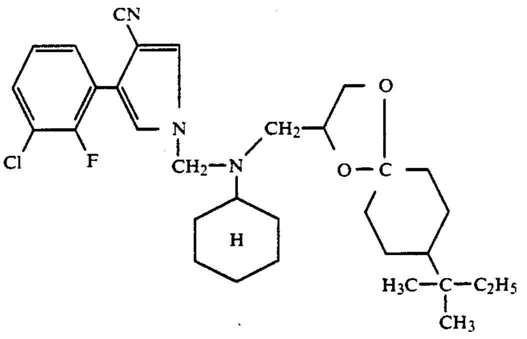

or an acid addition salt thereof.

5. A compound according to claim 1, wherein such compound is 4-cyano-3-(2,3-dichlorophenyl)-1-(N-cyclohexyl-1, 4-dioxaspiro[4.5]decane-8-(1,1-dimethylpropyl)-2-methaneaminomethyl)-pyrrole of the formula

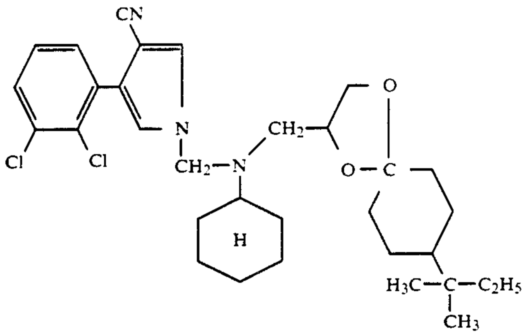

or an acid addition salt thereof.

6. A compound according to claim 1, wherein such compound is 4-cyano-3-(2-methyl-3-trifluoromethyl)-1-(N-methoxypropyl-1,4-dioxaspiro[4.5]decane-8-(1,1-dimethylpropyl)-2-methaneaminomethyl)-pyrrole of the formula

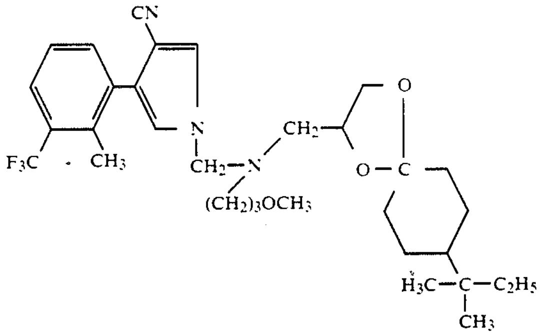

or an acid addition salt thereof.

7. A fungicidal or microbicidal composition comprising a fungicidally or microbicidally effective amount of a compound or acid addition product thereof according to claim 1 and a diluent.

8. A method of combating fungi or microbes which comprises applying to such fungi or microbes or to a habitat thereof a fungicidally or microbicially effective amount of a compound or acid addition product thereof according to claim 1.

9. The method according to claim 8, where such compound is 4-cyano-3-(2-fluoro-3-chlorophenyl)-1-(N-cyclohexyl-1,4-dioxaspiro[4.5]decane-8-(1, 1-dimethylpropyl)-2-methaneaminomethyl)-pyrrole 4-cyano-3-(2,3-dichlorophenyl)-1-(N-cyclohexyl-1,4-dioxaspiro[4.5]decane-8-(1, 1-dimethylpropyl)-2-methaneaminomethyl)-pyrrole or 4-cyano-3-(2-methyl-3-trifluoromethyl)-1-(N-methoxypropyl-1, 4-dioxaspiro[4.5]decane-8-(1,1-dimethyl-propyl) -2-methaneaminomethyl)-pyrrole, or an acid addition salt thereof.

* * * * *

UNITED STATES PATENT AND TRADEMARK OFFICE
CERTIFICATE OF CORRECTION

PATENT NO. : 5,118,702

DATED : June 2, 1992

INVENTOR(S) : WOLLWEBER ET SL

It is certified that error appears in the above-identified patent and that said Letters Patent is hereby corrected as shown below:

Col. 32 line 64 Before " represents " insert --$R^1$ --

Col. 33 line 17 Before " represents " insert --$R^2$ --

Col. 34 line 45 Delete "ethaneaminomethyl " and substitute -- methaneaminomethyl --

Col. 36 line 23 Delete " microbically " and substitue -- microbicidally --

Signed and Sealed this

Fifteenth Day of March, 1994

Attest:

Bruce Lehman

BRUCE LEHMAN

*Attesting Officer* *Commissioner of Patents and Trademarks*